(12) United States Patent
Moumene et al.

(10) Patent No.: US 8,308,770 B2
(45) Date of Patent: Nov. 13, 2012

(54) DYNAMIC STABILIZATION SYSTEM

(75) Inventors: Missoum Moumene, Newton, MA (US); Martin Masson, Keller, TX (US)

(73) Assignee: DePuy Spine, Inc., Raynham, MA (US)

( * ) Notice: Subject to any disclaimer, the term of this patent is extended or adjusted under 35 U.S.C. 154(b) by 572 days.

(21) Appl. No.: 11/534,391

(22) Filed: Sep. 22, 2006

(65) Prior Publication Data

US 2008/0097434 A1    Apr. 24, 2008

(51) Int. Cl.
*A61B 17/70* (2006.01)

(52) U.S. Cl. .......................... 606/257; 606/255

(58) Field of Classification Search .................. 606/246, 606/53–60, 250–279, 280–299; 623/17.11, 623/17.13, 17.15–17.16; 248/65, 74.1
See application file for complete search history.

(56) References Cited

U.S. PATENT DOCUMENTS

| | | | | |
|---|---|---|---|---|
| 3,385,545 A * | 5/1968 | Patton | ........................... | 248/68.1 |
| 4,905,679 A * | 3/1990 | Morgan | ........................... | 606/70 |
| 5,336,224 A * | 8/1994 | Selman | ........................... | 606/280 |
| 5,593,143 A * | 1/1997 | Ferrarin | ........................... | 256/68 |
| 5,669,590 A * | 9/1997 | Przewodek | ........................... | 248/68.1 |
| 5,752,958 A * | 5/1998 | Wellisz | ........................... | 606/285 |
| 5,984,925 A * | 11/1999 | Apgar | ........................... | 606/284 |
| 6,149,651 A * | 11/2000 | Drewry et al. | ........................... | 606/60 |
| 6,267,764 B1 | 7/2001 | Elberg | | |
| 6,355,039 B1 * | 3/2002 | Troussel et al. | ........................... | 606/264 |
| 6,605,091 B1 * | 8/2003 | Iwanski | ........................... | 606/74 |
| 6,669,731 B2 * | 12/2003 | Ralph et al. | ........................... | 623/17.13 |
| 6,783,101 B2 * | 8/2004 | Knotts | ........................... | 248/68.1 |
| 6,960,211 B1 * | 11/2005 | Pfefferle et al. | ........................... | 606/282 |
| 7,007,900 B2 * | 3/2006 | Goodwin et al. | ........................... | 248/68.1 |
| 7,074,239 B1 * | 7/2006 | Cornwall et al. | ........................... | 623/17.11 |
| 7,297,146 B2 * | 11/2007 | Braun et al. | ........................... | 606/279 |
| 7,326,210 B2 | 2/2008 | Jahng | | |
| 7,621,912 B2 | 11/2009 | Harms | | |
| 7,621,940 B2 | 11/2009 | Harms | | |
| 7,682,375 B2 | 3/2010 | Ritland | | |
| 7,722,649 B2 | 5/2010 | Biedermann | | |
| 8,012,179 B2 * | 9/2011 | Bruneau et al. | ........................... | 606/257 |
| 2003/0144665 A1 * | 7/2003 | Munting | ........................... | 606/61 |
| 2003/0171749 A1 * | 9/2003 | Le Couedic et al. | ........................... | 606/61 |
| 2004/0002708 A1 | 1/2004 | Ritland | | |
| 2004/0049190 A1 | 3/2004 | Biedermann | | |
| 2004/0087949 A1 * | 5/2004 | Bono et al. | ........................... | 606/61 |
| 2004/0153155 A1 * | 8/2004 | Chung et al. | ........................... | 623/17.11 |
| 2004/0236327 A1 * | 11/2004 | Paul et al. | ........................... | 606/61 |
| 2005/0015090 A1 * | 1/2005 | Silverman | ........................... | 606/71 |
| 2005/0085815 A1 | 4/2005 | Harms | | |
| 2005/0131407 A1 * | 6/2005 | Sicvol et al. | ........................... | 606/61 |
| 2005/0154390 A1 | 7/2005 | Biedermann | | |
| 2005/0182401 A1 * | 8/2005 | Timm et al. | ........................... | 606/61 |
| 2005/0182409 A1 * | 8/2005 | Callahan et al. | ........................... | 606/72 |
| 2005/0203517 A1 | 9/2005 | Jahng | | |
| 2005/0203519 A1 * | 9/2005 | Harms et al. | ........................... | 606/61 |

(Continued)

FOREIGN PATENT DOCUMENTS

GB    2125295 A  *  3/1984

(Continued)

*Primary Examiner* — Alvin Stewart
*Assistant Examiner* — Jerry Cumberledge

(57) ABSTRACT

The present invention relates to a dynamic stabilization system (DSS) having at least one rod having a ring formed therein ("the spring") and a pair of pedicle screws adapted for fixation to separate vertebrae.

11 Claims, 8 Drawing Sheets

U.S. PATENT DOCUMENTS

| | | | |
|---|---|---|---|
| 2005/0247829 A1* | 11/2005 | Low et al. | 248/68.1 |
| 2005/0277935 A1* | 12/2005 | Morrison et al. | 606/61 |
| 2005/0288670 A1 | 12/2005 | Panjabi | |
| 2006/0009768 A1* | 1/2006 | Ritland | 606/61 |
| 2006/0064090 A1* | 3/2006 | Park | 606/61 |
| 2006/0142760 A1* | 6/2006 | McDonnell | 606/61 |
| 2006/0184171 A1* | 8/2006 | Biedermann et al. | 606/61 |
| 2006/0229608 A1* | 10/2006 | Foster et al. | 606/61 |
| 2006/0235396 A1* | 10/2006 | Sanders et al. | 606/69 |
| 2006/0235397 A1* | 10/2006 | Sanders et al. | 606/69 |
| 2006/0276790 A1* | 12/2006 | Dawson et al. | 606/61 |
| 2007/0016193 A1* | 1/2007 | Ritland | 606/61 |

FOREIGN PATENT DOCUMENTS

| | | | |
|---|---|---|---|
| GB | 2438502 | * | 5/2007 |
| WO | WO 9940866 A1 | * | 8/1999 |
| WO | WO 03/007831 | * | 1/2003 |
| WO | WO 2007/138270 | * | 12/2007 |

* cited by examiner

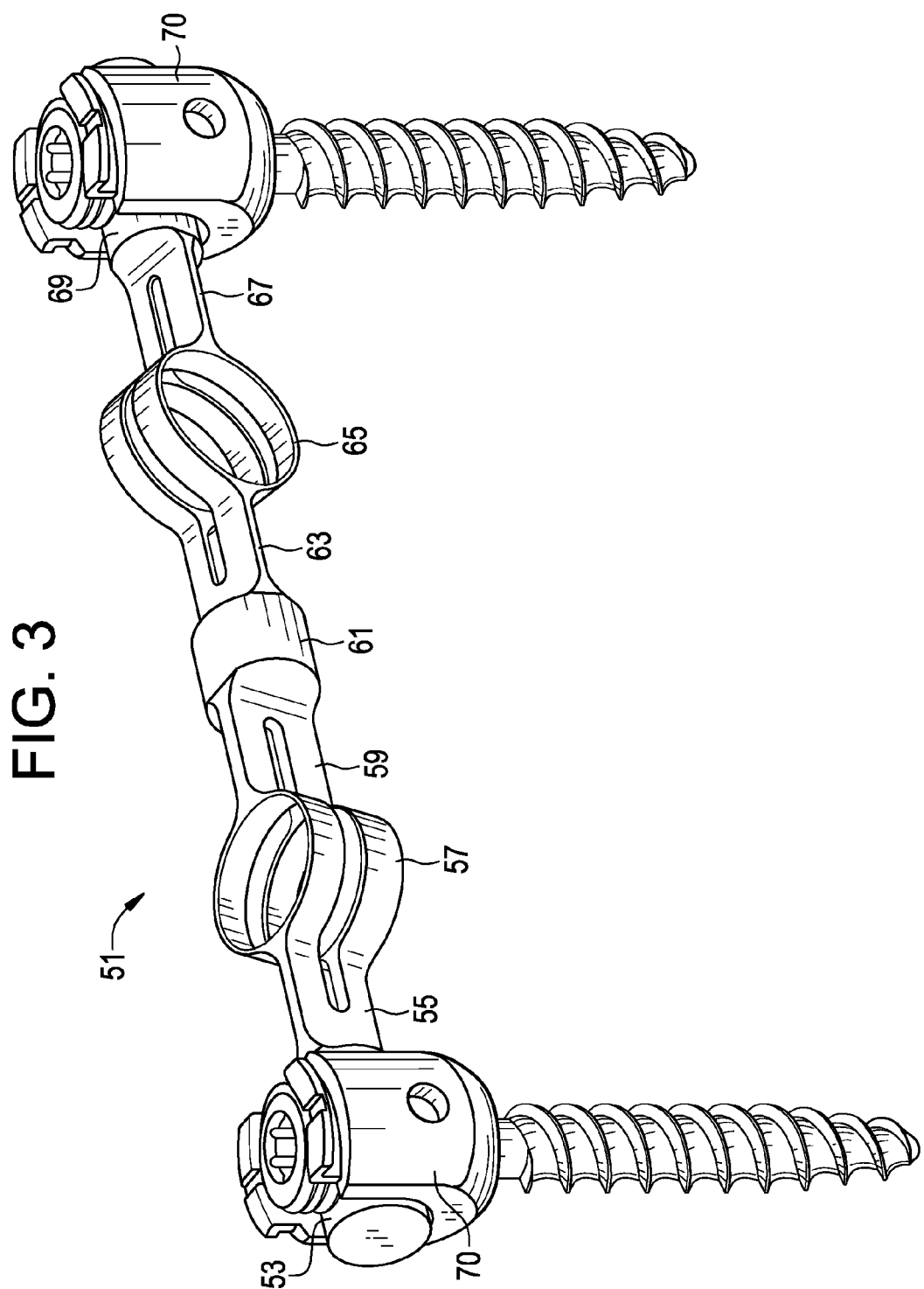

Torsion

Compression

Lateral Bending

Flexion

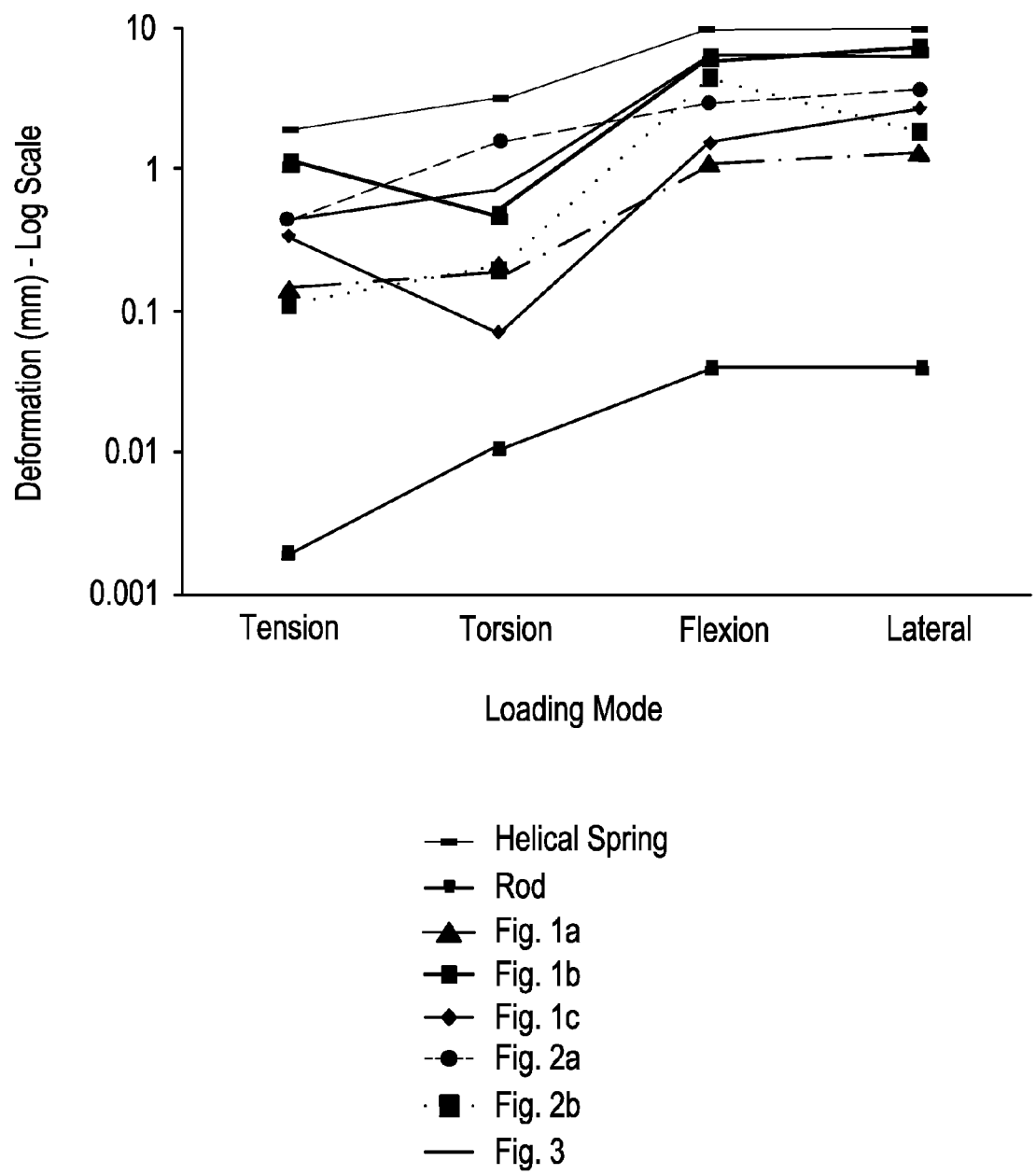

DYNAMIC STABILIZATION SYSTEM

BACKGROUND OF THE INVENTION

Conventional methods of spinal fixation utilize a system comprising a set of pedicle screws and a set of rigid, metallic rods to stabilize one or more vertebra. Permanent immobilization of one or more functional segmental units (FSU) is the desired clinical outcome for such procedure.

Although stabilization of the spine is the main objective of the fixation, immobilization of the spine with stiff, non-compliant bars or rods is known to have adverse side effects. Among them, stress shielding and changes in the loading patterns on the facets and other supporting spinal structures have been reported.

One of the reasons titanium is often selected over stainless steel as the rod material is its lower elastic modulus. Having a lower stiffness allows the titanium rod to bend and flex a little more than its stainless steel counterpart, somewhat limiting stress shielding and sparing the facets (although not by a great measure). Thus, it must be recognized that the biomechanical advantage of the titanium rod is minor and consequently the need for a more compliant system is not truly addressed.

Therefore, to further provide limited mobility to the FSU, reduce stress shielding, and reduce unwanted loads on the supported spinal structures, a more drastic approach than a simple change in the material composition is needed.

To solve the above-described problems associated with rigid fixation, dynamic stabilization devices have been developed. Although the majority of these devices provide added flexibility, their applicability can be limited due to the shortcomings in their spring design, with the majority providing added compliance in flexion-extension but lacking torsional stiffness, a pre-requisite for a well-controlled stability.

In order to mimic the physiologic spine, rods having spring components must provide the appropriate stiffness in flexion-extension, lateral bending, and compression-distraction. To do so, the spring system must have individually tuned translational and rotational springback properties.

A well-designed dynamic system should reflect a compromise between stiffness and compliance—not so stiff as not to load the adjacent structures, but not so compliant as to fail to provide the required stabilization. Thus, it is an object of the present invention to provide a mechanism for harmonious load-sharing between the biological structures.

Examination of prior art devices reveals shortcomings in attaining this goal:

U.S. Published Patent Application Numbers US20040049190A1 ("Biedermann I"), US20050085815A1 ("Harms I"), and US20050154390A1 (Biedermann II) suggest that the elastic section of the rod "be implemented in the form of a helical spring". A similar device is disclosed in U.S. Published Patent Application Number 20050203517A1 ("Jahng"). These devices are flexible, but they are not well-suited for resisting lateral forces or torsional moments.

U.S. Published Patent Application Numbers US20050288670A1 ("Panjabi") discloses a dynamic stabilization device "including overhanging stabilizing member". However, this device is cumbersome and complex, requiring several individual parts for the fabrication of a "shock absorber like" spring. The benefits of the device are limited to translational flexibility.

U.S. Published Patent Application Numbers US20040002708A1 ("Ritland") discloses a novel dynamic fixation device wherein the rod has a ring provided therein. However, this patent document is primarily concerned with providing structural support that "limits the amount of translation motion beyond normal physiological limits". Moreover, the large aspect ratio of the ring has the potential for impinging on surrounding tissues and may present challenges to the surgeon who desires to minimize harm to soft tissues (such as muscles and the like).

U.S. Published Patent Application Number US20050203519A1 ("Harms II") discloses a rod-shaped element that allows for a controlled motion of the parts to be stabilized relative to each other so that the "flexural motion is adjusted separately from the adjustment of the mobility in the axial direction". However, this device falls short by failing to include a mechanism for controlling rotational stiffness, which, if not properly selected, may prevent the device from functioning flawlessly.

U.S. Pat. No. 6,267,764 ("Elberg") discloses spine stabilization system having a pair of pedicle screws and a rod having an open ring therein. This design has the disadvantage in that the open nature of the ring does not adequately resist torsion.

SUMMARY OF THE INVENTION

It is the belief of the present inventors that by redesigning the rods of a spinal stabilization device so that their stiffness is markedly reduced, side effects caused by stiff rods can be substantially alleviated.

The present invention relates to a dynamic stabilization system (DSS). It comprises at least one rod having a ring formed therein ("the spring") and a pair of pedicle screws adapted for fixation to separate vertebrae. While the pedicle screws are of the conventional type, the cornerstone of the invention is an enhanced spring with improved performances for dynamic stabilization.

In a preferred embodiment, two springs are used along with four pedicle screws to stabilize one FSU. Preferably, each pedicle screw/spring/pedicle screw assembly is affixed laterally on each side of the spine, when viewed in the frontal plane. Each assembly joins at least two separate vertebrae, i.e.: one pedicle screw is affixed to one vertebra while the other pedicle screw is affixed to another separate vertebra with the spring spanning both vertebrae.

Each spring has two rod-like end portions and a central section containing a ring. The end portions of the springs are such that their attachment to commercially available pedicle screws is easily accomplished. The spring's rod-like end portions are generally cylindrical in shape with a diameter in the 3-6 mm range. The end portions can be hollowed to take the form of a tube.

The central spring section is the "active" section of the device. The central section stretches and deforms under the application of single and complex loads, and provides the desired dynamism for this application.

The exact geometric dimensions of the ring dictate how much it deforms under a given applied load. While the ring's main function is to provide a desired stiffness under compressive and tensile loads, the ring also deforms when subject to torsional moments, flexing moments, or any combination of the above.

Therefore, in accordance with the present invention, there is provided a dynamic stabilization system for stabilizing the spine, comprising:

a) a pair of bone anchors, each anchor adapted for fixation to an independent vertebra, and
b) a link member adapted to interconnect the anchor members, the link member comprising a first end portion, a second end portion and a closed ring therebetween.

DESCRIPTION OF THE FIGURES

FIG. 3 discloses a link members of a dynamic stabilization system of the present invention, having two pair of closed rings oriented 90 degrees from each other.

FIG. 5 discloses a graph displaying the relative deformations of various devices corresponding to specific loading mode, expressed on a log scale.

DETAILED DESCRIPTION OF THE INVENTION

Figure 1A:
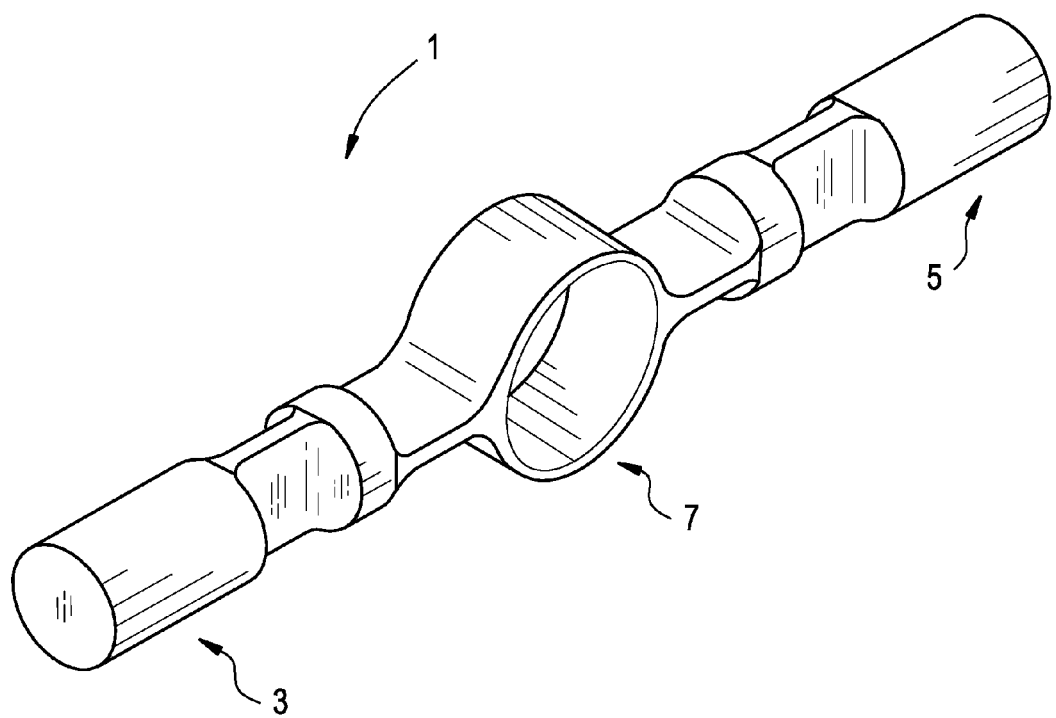
FIGS. 1a-1c disclose link members of a dynamic stabilization system of the present invention, each having a closed ring.

Now referring to FIG. 1a, there is provided a dynamic stabilization system for stabilizing the spine, comprising:
 a) a pair of bone anchors (not shown), each anchor adapted for fixation to an independent vertebra, and
 b) a link member 1 adapted to interconnect the anchor members, the link member comprising a first end portion 3, a second end portion 5 and a closed ring 7 therebetween.

In this embodiment, the first and second end portions are cylindrical and form a longitudinal axis, while the closed ring has an axis that is perpendicular to the longitudinal axis.

The materials for the springs are preferably the same as those used in the manufacturing of the pedicle screws, namely, Ti-6Al-4V, cobalt-chrome, or stainless steel. Alternatively, shape memory alloys such as 50% Ni-50% Ti can be used, as well as shape memory polymers or composite materials or any other type of biocompatible materials as long as the resulting stiffness and device dimensions are compatible with pre-set design constraints and performance criteria.

The ring is generally closed, and is oval, elliptical, or preferably, circular in shape. Preferably, the ring is essentially a circular element with a through hole. The hole is generally circular but may be of a different shape (oval, square, cloverleaf, etc). The sides of the ring are generally flat in a direction parallel to the ring's axis but may take the form of an O-ring (a donut) or any other closed form topology (triangular, square, pentagonal, hexagonal, etc.).

In one embodiment, the ring component of the present invention has a thickness (measured in a direction perpendicular to the ring's axis) that is less than its depth (measured in a direction of the ring's axis). Because the thickness of the ring is a design variable that controls the stiffness of the device, this thin ring embodiment is advantageous because it is more flexible and so controls stiffness.

Therefore, in accordance with the present invention, there is provided a dynamic stabilization system for stabilizing the spine, comprising:
 a) a pair of bone anchors, each anchor adapted for fixation to an independent vertebra, and
 b) a link member adapted to interconnect the anchor members, the link member comprising a first end portion, a second end portion and a ring therebetween,
wherein the ring has a thickness and a depth, and the depth of the ring is greater than the thickness of the ring.

For example, in one preferred embodiment of the thin ring, the ring has the following dimensions: OD=10 mm, ID=9.25, thickness in a direction perpendicular to the ring's axis: 0.375 mm, depth in a direction of the ring's axis: 5.2 mm. Computer simulations suggest that a ring manufactured to these dimensions and made out of Ti-6Al-4V would deform about 0.16 mm per 100 N applied (0.32 mm deformation under 200 N). In contrast, a rod would deform about 0.001 mm per 100 N applied (160 times stiffer) and a equivalent helical spring would deform approximately 0.95 mm per 100 N (6 times more flexible). Therefore, such a ring provides the desired biomechanical compromise discussed above.

In some preferred embodiments, the ring has a first diameter and a cylindrical end portion has a second diameter, and the ratio of the first diameter to the second diameter is between 1:1 and 3:1, more preferably between 1:1 and 2:1. In this embodiment, the ration is sufficiently small to prevent impinging on surrounding tissues to minimize harm to soft tissues.

Although the central section of the spring is often made out of at least one sub-section, it may also comprise several sub-sections, with each having a geometry specifically designed for a specific purpose. For example, while a single closed ring may provide the some desirable characteristics, in some cases it may be advantageous to have a multiplicity of rings. The rings can be placed in series, in parallel, or both.

The benefits of providing a stabilization device having a plurality of rings are many fold. For example, in a first embodiment, at least two rings are placed in series and a lower stiffness can be achieved using the same ring diameter as opposed to a single ring. Alternatively, serial rings may be provided with a smaller diameter to achieve the same stiffness as the single ring, while also allowing their insertion through a more minimally invasive procedure that relies upon the device being introduced through a more narrow passage.

In another embodiment in which two rings in series are utilized, the first ring is oriented as previously described (where its axis is perpendicular to the longitudinal axis of the linking member) and the other ring is oriented at about ninety degrees with respect to the first ring (wherein the axis of the second ring is likewise perpendicular to the longitudinal axis of the linking member). The embodiment provides the advantage of providing substantially the same bending properties in two normally-disposed planes.

In a second embodiment, a ring may be slotted to create multiple rings placed in parallel. This design provides an alternative means of reducing stiffness.

In some cases, it may be advantageous to provide rings that have one or more cutouts or recesses, or rings that are made of mesh, to reduce the stiffness of the ring.

In one embodiment, as in FIG. 1, the ring is in line with the rod end portions and the general plane of the ring is oriented perpendicular to the plane passing through a line formed by the rod's end portions and the general direction of the pedicle screws. In other words, the axis of the ring is perpendicular to the longitudinal axis formed by the end portions.

In another embodiment, a ring is oriented at an angle of between about 0 and 90 degrees with respect to the longitudinal axis passing through the rod's end portions.

In accordance with the present invention, an infinite variety of angle selection is possible. Indeed, a single ring or a multiplicity of rings can be utilized and coupled in any imaginable 3D space configuration to obtain a desired effect, namely, a specific combination of stiffnesses in different planes.

In some embodiments, the center of the ring may be totally or partially filled with a resilient biocompatible material. The resilient biocompatible material further strengthens the construct by supporting the ring from the inside and providing added springback. The resilient material could be a polymer (such as polyurethane or PEEK) or a biocompatible gel such as those used in the manufacturing of artificial nucleuses. Conceivably, the material could be compressed into the ring-like cavity to provide additional springback properties.

Therefore, in accordance with the present invention, there is provided a dynamic stabilization system for stabilizing the spine, comprising:
 a) a pair of bone anchors, each anchor adapted for fixation to an independent vertebra, and
 b) a link member adapted to interconnect the anchor members, the link member comprising a first end portion, a second end portion and a ring therebetween having a center,
wherein the center of the ring is at least partially filled with a polymeric biocompatible material.

Aside from the ring-like section(s), the DSS comprises one or more transition sections. A transition section is defined as the region of the device that joins two or more rings together, or one ring to an end section of the spring. Two or more transition sections may also be placed in series, or in parallel with each other.

Although a transition section may be "passive" i.e.: it may not play an important role in controlling the device's deformation, the preferred mode will be an "active" one: preferably, the transition section will allow a certain deformation to occur under certain loads or moments, while restraining motion or deformation when loads and moments are applied in other planes.

For example, in a preferred embodiment, the rod-like extremity transitions into a bar of a substantially rectangular cross-section before joining a central ring. Other representative sections include an elliptical, diamond or dogbone section. This relatively flat transition section allows the device to flex more than it allows the device to bend laterally while providing adequate resistance in torsion.

Therefore, in accordance with the present invention, there is provided a dynamic stabilization system for stabilizing the spine, comprising:
 a) a pair of bone anchors, each anchor adapted for fixation to an independent vertebra, and
 b) a link member adapted to interconnect the anchor members, the link member comprising a first end portion, a second end portion, a ring therebetween and a first transition section therebetween, wherein the first transition section comprises a substantially rectangular cross section.

In addition, another flat section oriented at ninety degrees with respect to the above-mentioned transition section helps control an additional degree of freedom, namely, lateral bending (as opposed to rotation in the saggital plane, also known as flexion-extension motion).

Hence, a transition section may take the form of a flat bar twisted at an angle of, for example, thirty, forty five, sixty, ninety or one hundred and eighty degrees. In some embodiments, there is provided a substantially rectangular section that has been twisted about 90 degrees. This "twisted" section thus helps control bending in two normal planes.

Since the lateral and saggital deformations placed on the device differ depending upon the plane of flexion considered, it is advantageous to have distinct, physical transitional sections, for an independent control of motion in specific planes or about specific axes. In particular, since lateral and saggital ranges of motion are different, it is advantageous to have a distinct transition section for each to reflect these differences.

Conceivably, multiple transition sections can be included in the design of the DSS, based on a predetermined device stiffness. Different device stiffnesses may be required to treat different pathologies as well as different pathology grades.

ANSYS Workbench provided the framework for comparative assessment of performance. Several designs were evaluated (FIG. 1-3), each providing a specific deformation response. The responses (example given in FIGS. 4a-4d and 5) were compared to that of a plain, metallic rod (not shown) and to that of a helical spring-like design (not shown).

Of note, the DSS can be designed to cover a wide range of stiffnesses that fall in between that of a plain, metallic rod, and that of a helical spring-like design, thereby realizing the desirable compromise discussed above. The stiffnesses range from about one half to one twentieth that of a helical spring-like design, while still being ten or a hundred times more compliant than a plain, metallic rod (see FIG. 5).

Securing the link members of a dynamic stabilization system can be performed using threaded fasteners, taper locks, or other means of attachment. Generally, the surgeon will pay particular attention to the orientation the link members have with respect to the pedicle screws. Generally, the surgeon will follow a pre-determined assembly procedure in order to optimally orient the link members. Training can be provided to this effect. Alternatively, the device can be designed in such a way that only the link members can only be assembled in an optimal pre-determined orientation. In another embodiment, the surgeon may utilize visual clues such as color coded marks, etching, and the like, to ascertain whether the link members are being assembled in an optimal, pre-determined orientation.

Figure 1B:
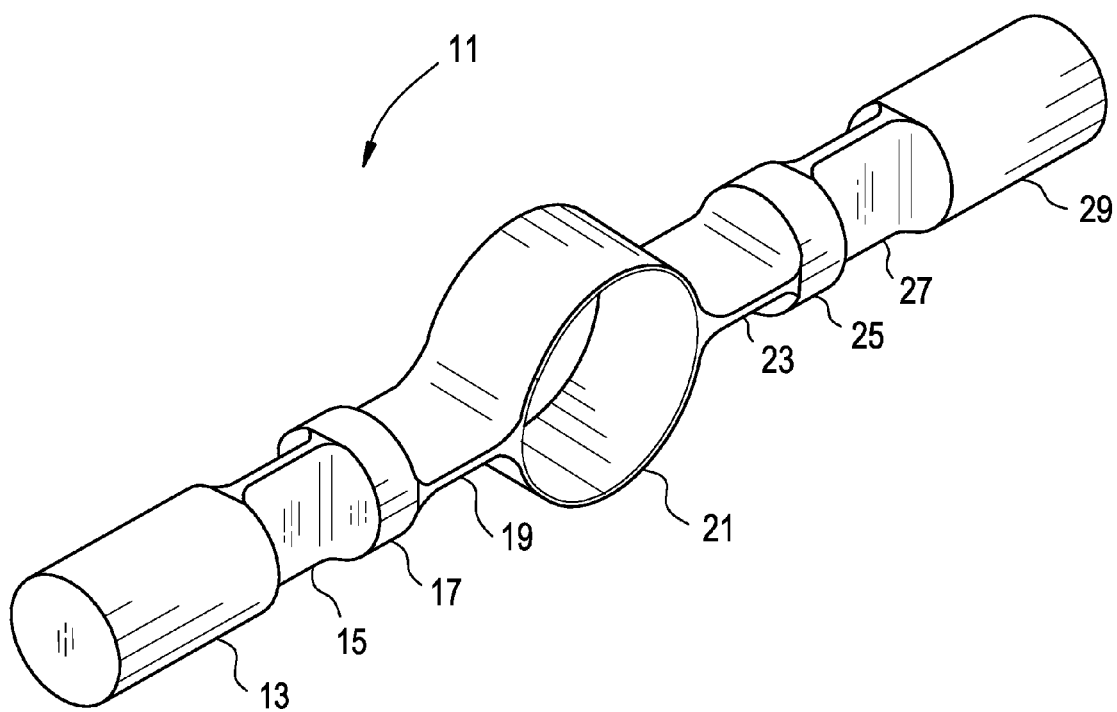

Now referring to FIG. 1b, there is provided a link member 11 comprising, in series:
 a) a first cylindrical end portion 13,
 b) a first transition section 15 having a substantially rectangular cross-section,
 c) a first cylindrical middle portion 17,
 d) a second transition section 19 having a substantially rectangular cross-section and oriented perpendicular with the first transition section,
 e) a thin circular ring 21,
 f) a third transition section 23 having a substantially rectangular cross-section and oriented perpendicular to the first transition section,
 g) a second cylindrical middle portion 25,
 h) a fourth transition section 27 having a substantially rectangular cross-section and oriented in line with the first transition section, and
 i) a second cylindrical end portion 29.

In this particular design of FIG. 1b, the ring has an about 10 mm diameter while the diameter of the cylindrical middle and end portions is about 5 mm.

The design of FIG. 1b differs from that of FIG. 1a in that the rectangular cross-sections of the transition sections of FIG. 1b are thinner. The design of FIG. 1b provides advantage in that it is more flexible than FIG. 1a.

Figure 1C:
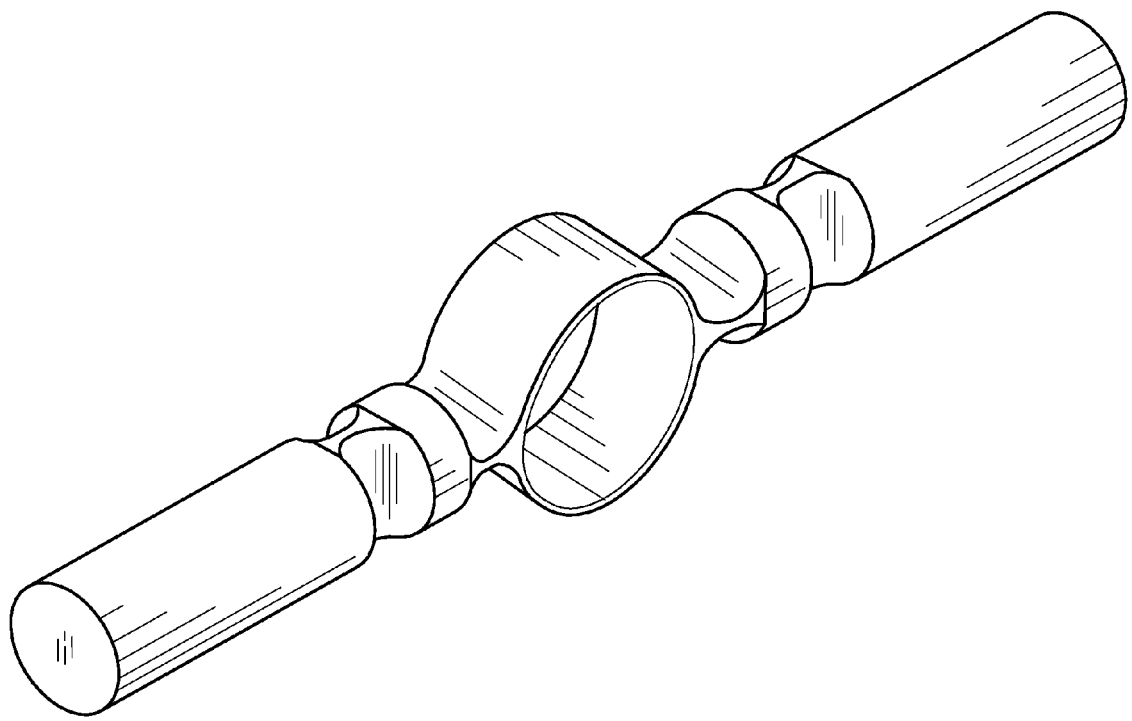

The design of FIG. 1c differs from that of FIG. 1a in that the lengths of the transition sections of FIG. 1c are shorter. The design of FIG. 1c provides advantage in that it is more compact than FIG. 1a, and therefore the rings can be larger for the same overall rod length.

Figure 2A:
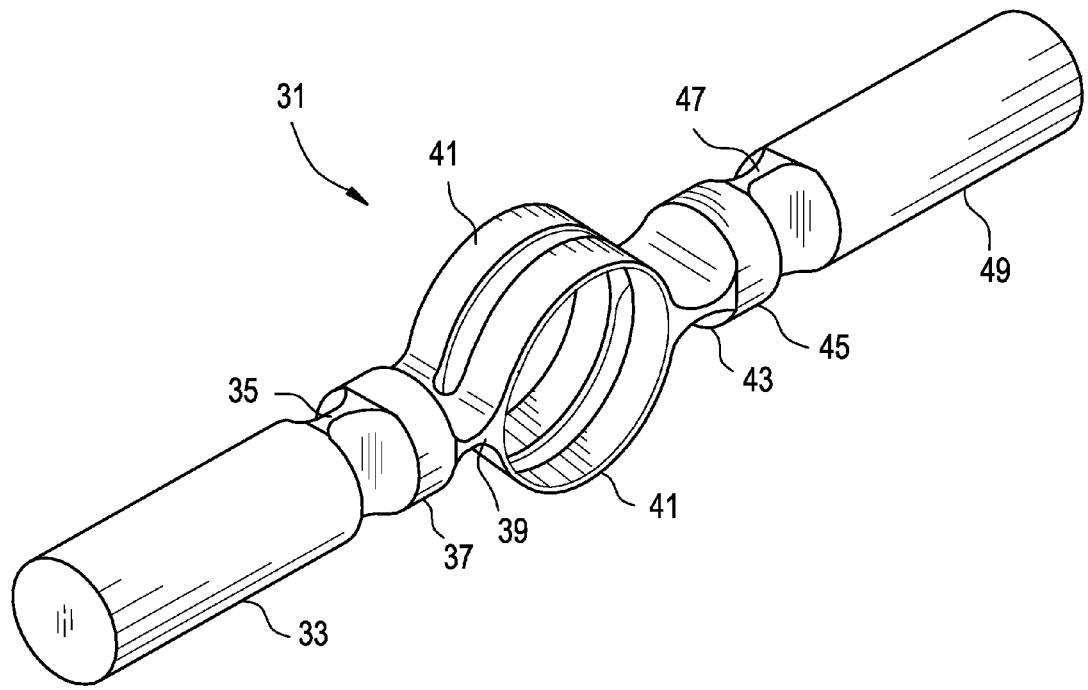
FIGS. 2a-2b disclose link members of a dynamic stabilization system of the present invention, each having a pair of closed rings.

Now referring to FIG. 2a, there is provided a link member 31 comprising, in series:
 a) a first cylindrical end portion 33,
 b) a first transition section 35 having a substantially rectangular cross-section,
 c) a first cylindrical middle portion 37,
 d) a second transition section 39 having a pair of substantially rectangular cross-sections and oriented perpendicular with the first transition section,
 e) a pair of thin circular rings 41, f) a third transition section 43 having a pair of substantially rectangular cross-sections and oriented perpendicular to the first transition section, g) a second cylindrical middle portion 45, h) a fourth transition section 47 having a substantially rectangular cross-section and oriented in line with the first transition section, and i) a second cylindrical end portion 49.

Figure 2B:
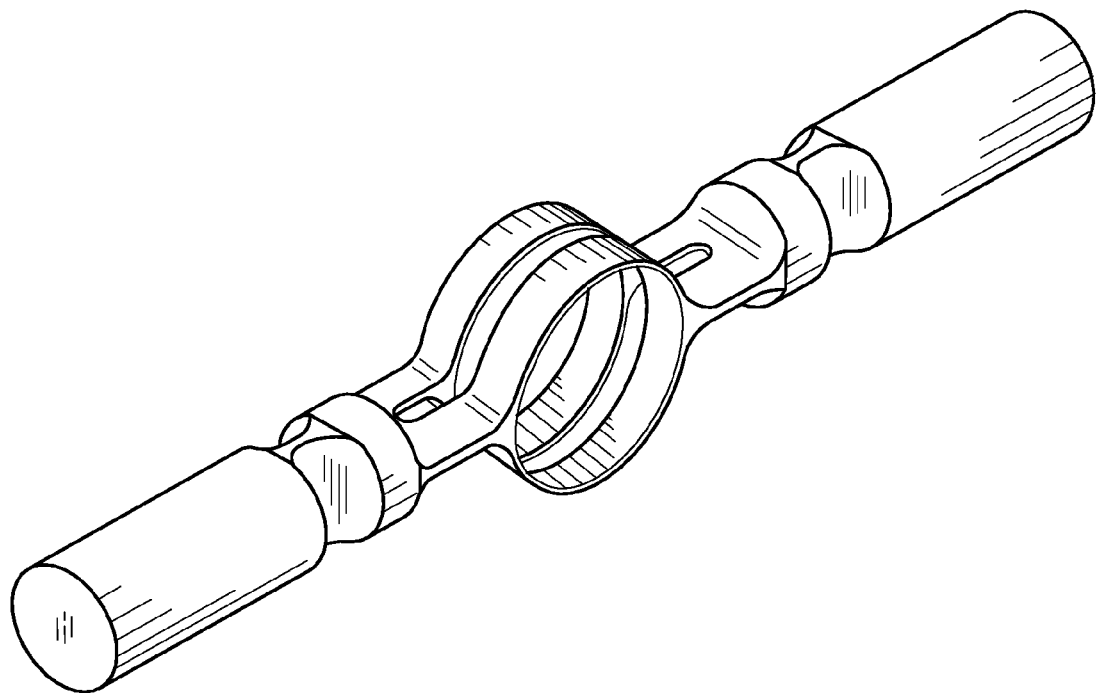

The design of FIG. 2*b* differs from that of FIG. 2*a* in that the diameter of the rings of FIG. 2*a* is larger.

Now referring to FIG. 3, there is provided a link member 51 comprising, in series:

a) a first cylindrical end portion 53, b) a first transition section 55 having a pair of substantially rectangular cross-sections, c) a first pair of circular rings 57 arranged in parallel, d) a second transition section 59 having a pair of substantially rectangular cross-sections and oriented in line with the first transition section, e) a cylindrical middle portion 61, f) a third transition section 63 having a pair of substantially rectangular cross-sections and oriented perpendicular to the first transition section, g) a second pair of circular rings 65 arranged in parallel and oriented perpendicular to the first pair of circular rings, h) a fourth transition section 67 having a pair of substantially rectangular cross-sections and oriented in line with the third transition section, and i) a second cylindrical end portion 69.

In this particular case of FIG. 3, the ring diameters are 7 mm while the diameters of the cylindrical middle and end portions is about 5 mm. Note that the pairs of rings are oriented at 90 degrees with respect to each other, as are the transition sections. In addition, FIG. 3 discloses terminal bone anchors 70 at either end of the rod.

Now referring to FIGS. 4*a*-4*d,* there is provided a depictions of the performance of the DSS of the present invention under various stresses.

Figure 4B:
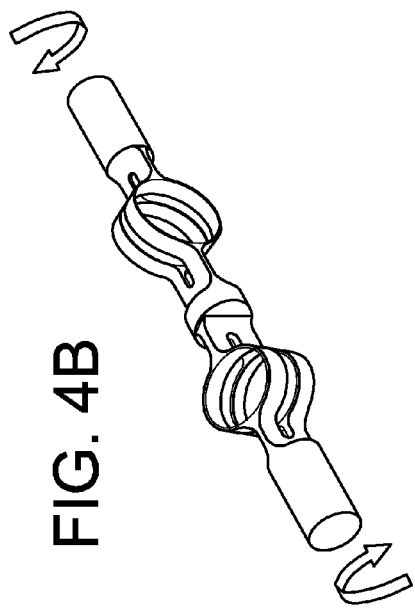
FIGS. 4a-4d disclose depictions of the performance of the link member of FIG. 3 under various loads.
Figure 4A:
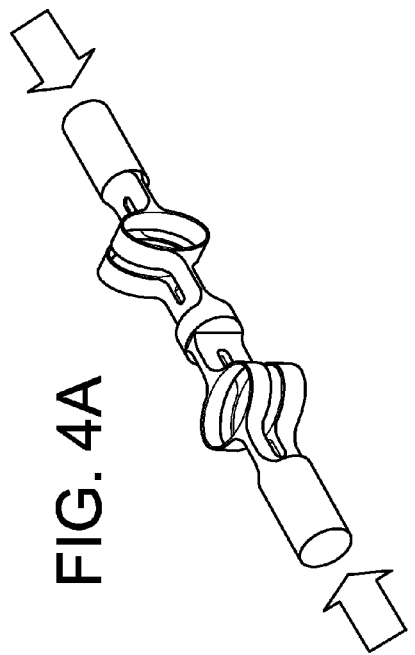
Figure 4D:
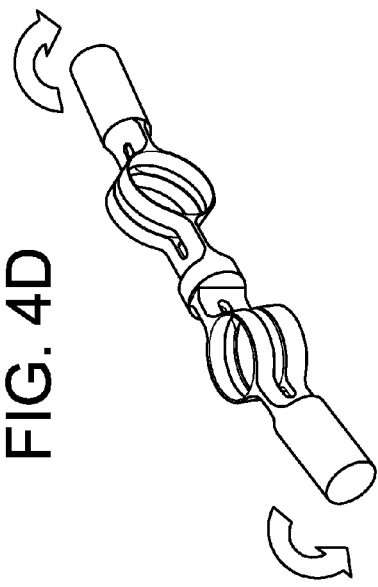

FIG. 4*a* shows the DSS of FIG. 3 under compression. Under compression, the circular rings deform to become oval.

FIG. 4*b* shows the DSS of FIG. 3 in torsion. In torsion, the inner transition zones radially deform so that one pair of circular rings rotates about the longitudinal axis of the link member.

Figure 4C:
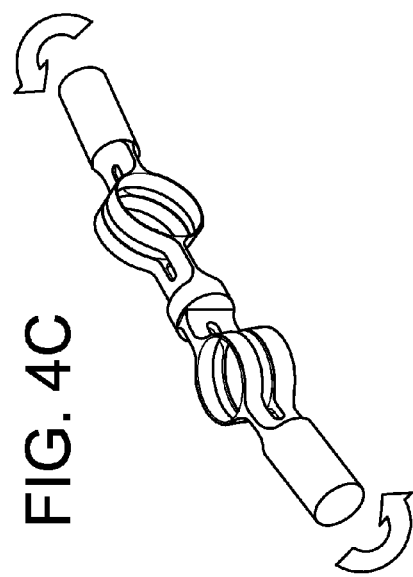

FIG. 4*c* shows the DSS of FIG. 3 in flexion. In flexion, the first and second transition zones bend so that the first pair of circular rings becomes angled with respect to the longitudinal axis of the link member.

FIG. 4*c* shows the DSS of FIG. 3 in lateral bending. In lateral bending, the third and fourth transition zones bend so that the second pair of circular rings becomes angled with respect to the longitudinal axis of the link member.

In FIG. 5, the helical spring performance is seen at the top of the chart while the plain rod performance is seen at the bottom of the chart. The range of deformation of the devices of the present invention falls in-between the former and the conventional devices and resides mostly in the upper-third of the graph.

We claim:

1. A dynamic stabilization system for stabilizing the spine, comprising:

a. a pair of bone anchors, each anchor adapted for fixation to an independent vertebra, and b. a link member rod adapted to interconnect the anchor members, the link member rod comprising a first end portion, a second end portion, a first ring therebetween and a second ring therebetween, wherein the first ring has a first planar lateral surface and a first plane extending through the first ring and parallel to the first planar lateral surface, and the second ring has a second planar lateral surface and a second plane extending through the second ring and parallel to the second planar lateral surface, and wherein the first plane is oriented at about ninety degrees with respect to the second plane, wherein the first and second end portions form a longitudinal axis, and the plane of each ring is substantially aligned with the longitudinal axis, wherein the longitudinal axis of the rod passes through the through hole of the first ring and wherein each end portion of the rod attaches to a respective bone anchor.

2. The system of claim 1 wherein the first and second ring are aligned in series along the link member rod.

3. The system of claim 1 further comprising a third ring disposed between the first and second end portions.

4. The system of claim 3 further comprising a fourth ring disposed between the first and second end portions.

5. The system of claim 1 further comprising a twisted transition section between the first and second ring.

6. The system of claim 1 further comprising first, second, third and fourth transition sections disposed between the end portions, wherein the first ring is disposed between the first and second transition sections, and the second ring is disposed between the third and fourth transition sections.

7. The system of claim 6 wherein the first transition section is oriented perpendicular to the second transition section, and the third transition section is oriented perpendicular to the fourth transition section.

8. The system of claim 1 wherein link member rod is made of a metal selected from the group consisting of Ti-6Al-4V, cobalt-chrome, or stainless steel.

9. The system of claim 1 wherein the bone anchors fixate upon substantially cylindrical end portions.

10. The system of claim 1 wherein at least one ring is a slotted ring.

11. A dynamic stabilization system for stabilizing the spine, comprising:

a. a pair of bone anchors, each anchor adapted for fixation to an independent vertebra, and b. a link member rod adapted to interconnect the anchor members, the link member rod comprising a first end portion, a second end portion, a first closed ring therebetween and a second closed ring therebetween, wherein the first ring has a first planar lateral surface and a first plane extending through the first ring and parallel to the first planar lateral surface, and the second ring has a second planar lateral surface and a second plane extending through the second ring and parallel to the second planar lateral surface, and wherein the first plane is oriented at about ninety degrees with respect to the second plane, wherein the longitudinal axis of the rod passes through the through hole of the first ring and wherein each end portion of the rod attaches to a respective bone anchor.

* * * * *